United States Patent [19]
Weaver et al.

[11] Patent Number: 5,496,315
[45] Date of Patent: Mar. 5, 1996

[54] MEDICAL ELECTRODE INSULATING SYSTEM

[75] Inventors: Drew D. Weaver; William S. Nettekoven, both of Sandy, Utah

[73] Assignee: MegaDyne Medical Products, Inc., Draper, Utah

[21] Appl. No.: 296,670

[22] Filed: Aug. 26, 1994

[51] Int. Cl.$^6$ ............................................. A61B 17/39
[52] U.S. Cl. ........................ 606/41; 606/45; 606/49
[58] Field of Search ................................. 606/32–52

[56]  References Cited

U.S. PATENT DOCUMENTS

| | | | |
|---|---|---|---|
| 2,102,270 | 12/1937 | Hyams | 606/49 |
| 4,074,718 | 2/1978 | Morrison, Jr. | 606/45 |
| 4,427,006 | 1/1984 | Nottke | 606/42 |
| 4,932,952 | 6/1990 | Wojciechowicz, Jr. | 606/49 |
| 4,936,842 | 6/1990 | D'Amelio et al. | 606/50 X |

FOREIGN PATENT DOCUMENTS

| | | | |
|---|---|---|---|
| 578584 | 6/1933 | Germany | 606/49 |
| 2120553 | 12/1983 | United Kingdom | 606/49 |

*Primary Examiner*—Stephen C. Pellegrino
*Assistant Examiner*—Michael Peffley
*Attorney, Agent, or Firm*—John L. Sigalos

[57] ABSTRACT

A medical electrode insulating configuration in which an insulating sleeve such as an "O" Ring is disposed within a recess adjacent the distal end of an electrosurgical pencil holder for an electrosurgical blade, tightly surrounding the electrosurgical blade when in place, thus preventing moisture migration along the blade within the holder that might otherwise develop an undesired electrical path for operating voltages.

16 Claims, 1 Drawing Sheet

1

MEDICAL ELECTRODE INSULATING SYSTEM

This invention relates to electrosurgery and more particularly to electrosurgical instruments adapted for holding and manipulating electrosurgical blades during electrosurgery.

BACKGROUND OF THE INVENTION

Proposals have heretofore been made for utilizing medical electrodes with sources of high frequency electrical power, illustrative of which are those set forth in U.S. Pat. No. 4,582,838. In the practice of modern surgical techniques, the use of electrosurgical procedures is often employed. In accordance with such procedures, a surgical blade or tip is customarily employed to make incisions, cut tissue and otherwise conduct the indicated procedure. In so doing, various small blood vessels are severed or invaded, with the resultant undesired flow of blood and/or other electrically conductive body fluids and/or fluids used in such procedures. Although such fluids when in contact with the blade or tip tend to be vaporized or coagulated by the electrical energy from the blade, it has been found that in some instances, some of the fluid remains liquid and tends to migrate along the blade or tip into the housing of the blade holder where in past instances it has sometimes provided an undesired electrical path that resulted in burns to the surgeon and/or patient. Accordingly, there has developed a need for an improved pencil/blade combination that prevents inward migration of body fluids to electrically live uninsulated regions.

BRIEF SUMMARY OF THE INVENTION

The proposals of the present invention envision an improved combination of pencil-type holder and blade/tip in which there is formed within and near the distal end of the holder/housing, a recess into which there is positioned an insulating seal such as an "O" ring that snugly engages the insulated exterior of the blade/tip, thereby blocking migration of fluid flow along the insulating coating of the blade/tip into the interior of the holder/housing to electrically live uninsulated regions.

OBJECTS AND FEATURES OF THE INVENTION

It is one general object of the invention to improve electrosurgical equipment.

It is another object of the invention to improve safety in use of electrosurgical equipment.

It is still another object of the invention to improve insulating characteristics in an electrosurgical pencil holder.

It is yet another object of the invention to facilitate improved insulating characteristics while retaining ease of blade/tip insertion and removal.

Accordingly, in accordance with one feature of the invention, a blade/tip holder is fitted with a recess adapted for receiving an insulating sleeve near the distal end of the holder, thereby facilitating deployment of an insulating element to prevent undesired migration of electrically conductive fluids along the surface of the blade/tip.

In accordance with another feature of the invention, the insulating element such as an "O" ring is positioned within the recess and is compressed in place, thus providing an effective fluid seal.

In accordance with still another feature of the invention, the interior dimension of the insulating element is tailored to be slightly smaller than the corresponding exterior dimension, e.g., diameter, of the blade/tip so as to facilitate insertion/removal with gentle pressure while at the same time providing sufficient compression to effectuate an effective fluid seal.

These and other objects and features of the invention will be apparent from the following detailed description, by way of a preferred example, with reference to the drawing.

DETAILED DESCRIPTION OF THE INVENTION

Figure 1:
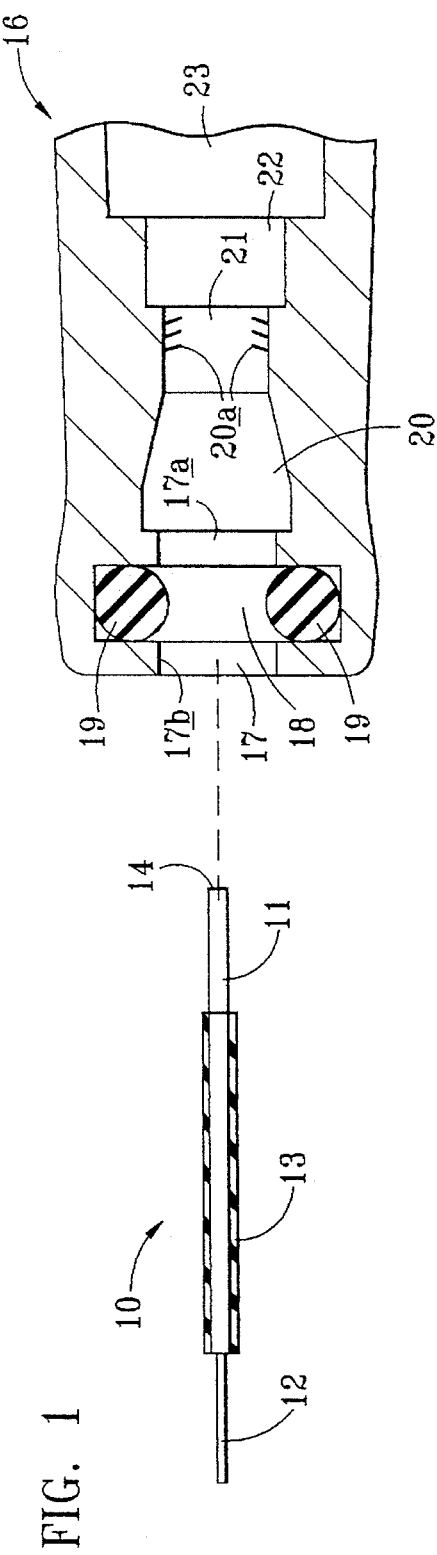
FIG. 1 is an exploded sectional view of the distal portion of an electrosurgical pencil and blade in which the pencil portion is enlarged to more clearly depict its geometries.

Now turning to the drawing, and more particularly FIG. 1 thereof, it will be seen to depict in section, a conventional electrosurgical electrode 10 having a principal structural central portion 11, a blade or other electrode configuration portion 12 extending from central portion 11, and an insulating coating or sleeve 13 surrounding the intermediate and distal end of central portion 12.

The distal end of pencil 16 may take any of a variety of conventional exterior geometries including that as shown. However, within such end there is provided an orifice 17 which is in spatial communication with recess 18 within which there is positioned an insulating seal such as "O" ring 19. Recess 18 is in spatial communication with a region 17a which, for convenience, is similar in dimensions to that of region 17. Connected with region 17a is region 20 which preferably is geometrically configured as shown. Thereafter, and progressing toward the proximal end (not shown) of the pencil 16 are a succession of interconnecting chambers 21, 22 and 23 which are provided with differing dimensions so as to mechanically support and hold (grip) the electrode and provide for electrical connection. These are described in greater detail below.

Figure 3:
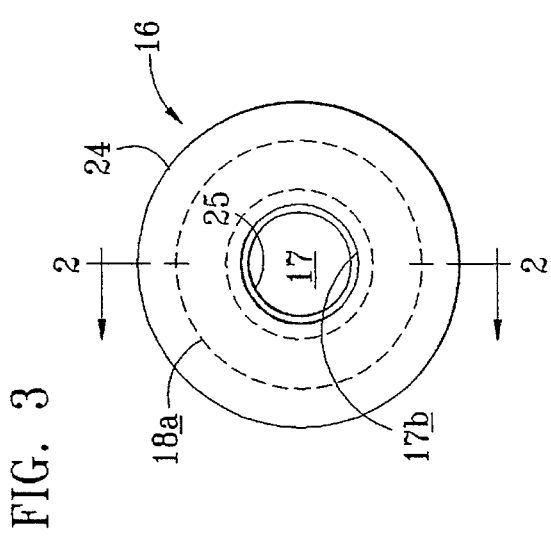
FIG. 3 is an end view of the distal end of the electrosurgical pencil.

Now turning to FIG. 3, it will be seen to be a view of the distal end of the pencil. There, it will be seen, the exterior 24 of the pencil 16 is illustrated as being essentially circular. However, it will be recognized by those skilled in the art that other exterior geometrical shapes could readily be employed. Thus, for example, an oval, square, rectangular or trapezoidal exterior geometrical shape could be employed provided that an interior recess such as recess 18 was included.

In FIG. 3, the dashed circle identifies surface 18a, and 17b the inner surface of orifice 17. Circular surface 25 defines the inner surface of region 21.

Figure 2:
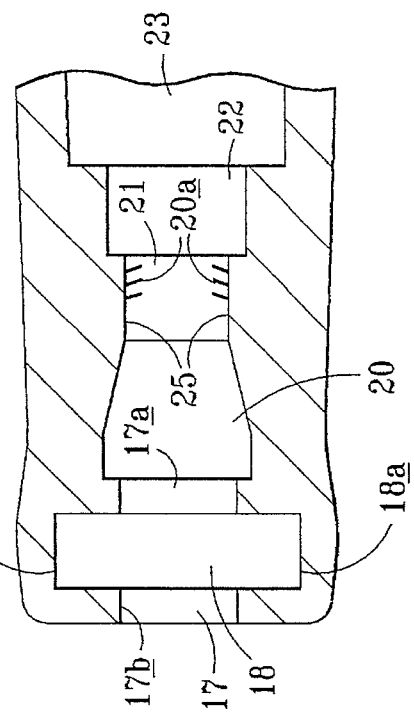
FIG. 2 is a sectional view of the distal portion of the electrosurgical pencil without the "O" ring in position.

In region 20 (FIGS. 1 and 2) there are provided some small resilient "teeth" 20a angled toward the distal end of the pencil 16 to grip the insulation 13. These small teeth help to secure the electrode 10 to prevent it from disengaging and rotating.

Chamber 21 preferably is the same diameter as chamber 17/17a to support the electrode 10. Chamber 22 is a receptacle for a conventional electrical connector (not shown), and chamber 23 is a hollow section within the pencil case to maintain uniform wall thickness. It's inside surface preferably should parallel the outside of the case.

Although the dimensions of pencil 16 are enlarged so as to provide additional clarity of presentation, it should be noted that in practice the inner diameter of insulating "O" ring is slightly smaller than the external diameter of insulating coating 13, thus ensuring a snug fit when the blade 10 is inserted into its place within pencil 16. Because of this difference in dimensions, insertion of the blade deforms the resilient material of the "O" ring slightly and forms a tight seal that prevents fluid or moisture from progressing further inward into the interior of the pencil and thus maintains the insulating integrity of the combination pencil/blade.

It will now be evident to those skilled in the art that there has been described herein an improved electrosurgical pencil and blade that prevents undesired fluid migration while preserving ease of blade installation and removal.

Although the invention hereof has been described by way of example of a preferred embodiment, it will be evident that other adaptations and modifications can be employed without departing from the spirit and scope thereof. For example, for an unusually severe environment an additional "O" ring could be employed in a position longitudinally spaced from that of "O" ring 19, thus providing additional protection against undesired fluid migration.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. An electrosurgical pencil comprising:
   (a) an elongated housing having a proximal end and a distal end;
   (b) an elongated longitudinally disposed interior chamber within said elongated housing, said interior chamber having mounted on its interior walls a plurality of flexible teeth members extending only partially from said walls toward the center of said chamber;
   (c) an orifice in said distal end communicating with said interior chamber;
   (d) means in said housing including said orifice for receiving and disengageably mounting an elongated electrosurgical instrument having a proximal end, a distal end, a first region at said proximal end of said instrument for making electrical connection to said instrument, and an electrically insulating coating extending from said first region toward said distal end of said instrument, said insulating coating ending before said distal end of said instrument; and
   (e) means including an elastomeric insulating sleeve disposed within said housing adjacent said orifice and in spatial communication with said orifice and said interior chamber effective when said proximal end of said instrument is positioned within said distal end of said housing for sealing said instrument around said electrically insulating coating to prevent migration of fluid from without said housing past said insulating coating.

2. An electrosurgical pencil according to claim 1 wherein said insulating sleeve is an annular member.

3. An electrosurgical pencil according to claim 2 wherein said insulating sleeve fits contiguously within an inner surface of said elongated housing adjacent said orifice.

4. An electrosurgical pencil according to claim 1 wherein said insulating sleeve is an "O" ring.

5. An electrosurgical pencil according to claim 4 wherein said "O" ring fits contiguously within an inner surface of said elongated housing adjacent said orifice.

6. An electrosurgical pencil according to claim 1 wherein said flexible teeth members are inclined at an angle with respect to said walls and are tilted toward said proximal end.

7. In combination, an electrosurgical pencil and surgical blade comprising:
   (a) an elongated housing having a proximal end and a distal end,
   (b) an elongated longitudinally disposed interior chamber within said elongated housing said interior chamber having mounted on walls of said chamber a plurality of flexible teeth members extending only partially from said walls toward the center of said chamber and engaging said elongated electrosurgical blade;
   (c) an orifice in said distal end communicating with said interior chamber;
   (d) an insulating sleeve disposed within said housing immediately adjacent said orifice and in spatial communication with said orifice and said interior chamber; and
   (e) an elongated electrosurgical blade having proximal end, a distal end, a first region at said proximal end of said blade for making electrical connection to said blade, and an electrically insulating coating extending from said first region toward said distal end for a sufficient length so that said electrically insulating coating is in fluid sealing contact with said insulating sleeve when said proximal end of said blade is mounted within said interior chamber and passed through said insulating sleeve.

8. A combination according to claim 7 in which said insulating sleeve is resilient.

9. A combination according to claim 7 in which said insulating sleeve is an annular member.

10. A combination according to claim 7 in which said insulating sleeve fits contiguously with an inner surface of said elongated housing adjacent said orifice.

11. A combination according to claim 10 in which said insulating sleeve is an "O" ring.

12. A combination according to claim 11 wherein the exterior dimension of said electrically insulating coating on said elongated electrosurgical blade is larger than the interior diameter of said "O" ring, thereby compressing said "O" ring to fit tightly against said electrically insulating coating on electrosurgical blade and the adjacent interior surface of said elongated chamber, thereby tightly sealing said electrosurgical blade within said electrosurgical pencil to prevent passage of fluids thereby.

13. A combination according to claim 7 in which said insulating sleeve is an "O" ring.

14. A combination according to claim 7 wherein said flexible teeth members are inclined at an angle with respect to said walls and are tilted toward said proximal end.

15. A combination according to claim 7 wherein the exterior dimension of said electrically insulating coating on said elongated electrosurgical blade is larger than the interior dimension of said insulating sleeve, thereby compressing said insulating sleeve to fit tightly around said electrically insulating coating.

16. In combination, an electrosurgical pencil and surgical blade comprising:
   (a) an elongated housing having a proximal end and a distal end;

(b) an elongated longitudinally disposed interior chamber within said elongated housing, said interior chamber having affixed to an inner surface thereof a plurality of flexible teeth extending only partially from said walls toward the center of said chamber and normally inclined toward said proximal end of said pencil;

(c) an orifice in said distal end communicating with said interior chamber;

(d) an "O" ring seal in contiguous sealing contact with an interior wall of said interior chamber and disposed within said housing adjacent said orifice and in spatial communication with said orifice and said interior chamber; and (e) an elongated electrosurgical blade having a proximal end, a distal end, a first region at said proximal end of said blade for making electrical connection to said blade, and an electrically insulating coating extending from said first region toward said distal end for a sufficient length so that when said proximal end of said blade is mounted within said interior chamber and passed through said "O" ring, said "O" ring is compressed into a tight sealing relationship with said insulating coating, said proximal end of said blade being further extended past said flexible teeth and in engagement therewith to impart to said teeth a bending moment to bend said teeth thereby to increase said inclination of said teeth toward said proximal end and hold said blade in place.

* * * * *